United States Patent [19]

Amblard et al.

[11] Patent Number: 4,567,749
[45] Date of Patent: Feb. 4, 1986

[54] PROCESS AND APPARATUS FOR DETERMINING THE INTERFACIAL AREA IN A TWO-PHASE MIXTURE INCORPORATING A GASEOUS PHASE FLOWING IN THE FORM OF BUBBLES

[75] Inventors: Alain Amblard, Lyons; Jean-Marc Delhaye; Favreau Claude, both of Grenoble, all of France

[73] Assignee: Commissariat a l'Energie Atomique, Paris, France

[21] Appl. No.: 597,038

[22] Filed: Apr. 5, 1984

[30] Foreign Application Priority Data

Apr. 20, 1983 [FR] France ............................... 83 06473

[51] Int. Cl.⁴ ...................... G01N 13/00; G01N 29/02
[52] U.S. Cl. .......................................... 73/19; 73/599
[58] Field of Search ................... 73/432 PS, 61 R, 19, 73/599

[56] References Cited

U.S. PATENT DOCUMENTS 2,573,390 10/1951 Blanchard ................................ 73/19
3,914,984 10/1975 Wade ..................................... 73/599
4,015,464 4/1977 Miller et al. .

4,327,587 5/1982 Docekal ................................. 73/599

FOREIGN PATENT DOCUMENTS 2244172 of 1975 France .

OTHER PUBLICATIONS

Heisig et al, An Ultrasonic Bubble Detector, Instrument Society of America, preprint No. 11.1-1-64, Oct. 12-15, 1964.

Primary Examiner—S. Clement Swisher
Attorney, Agent, or Firm—James E. Nilles

[57] ABSTRACT

Process for the determination of the interfacial area in a container containing a two-phase mixture incorporating a liquid phase and a gaseous phase flowing in the liquid phase in the form of bubbles. For a same path of a sequence of ultrasonic sound wave trains emitted at constant amplitudes in said container, the ratio of the mean values of the maximum amplitudes of the wave trains received after passing through the two-phase mixture and after passing through the liquid phase only is determined and the thus determined ratio is plotted on a calibration curve giving the interfacial area value as a function of this ratio.

3 Claims, 8 Drawing Figures

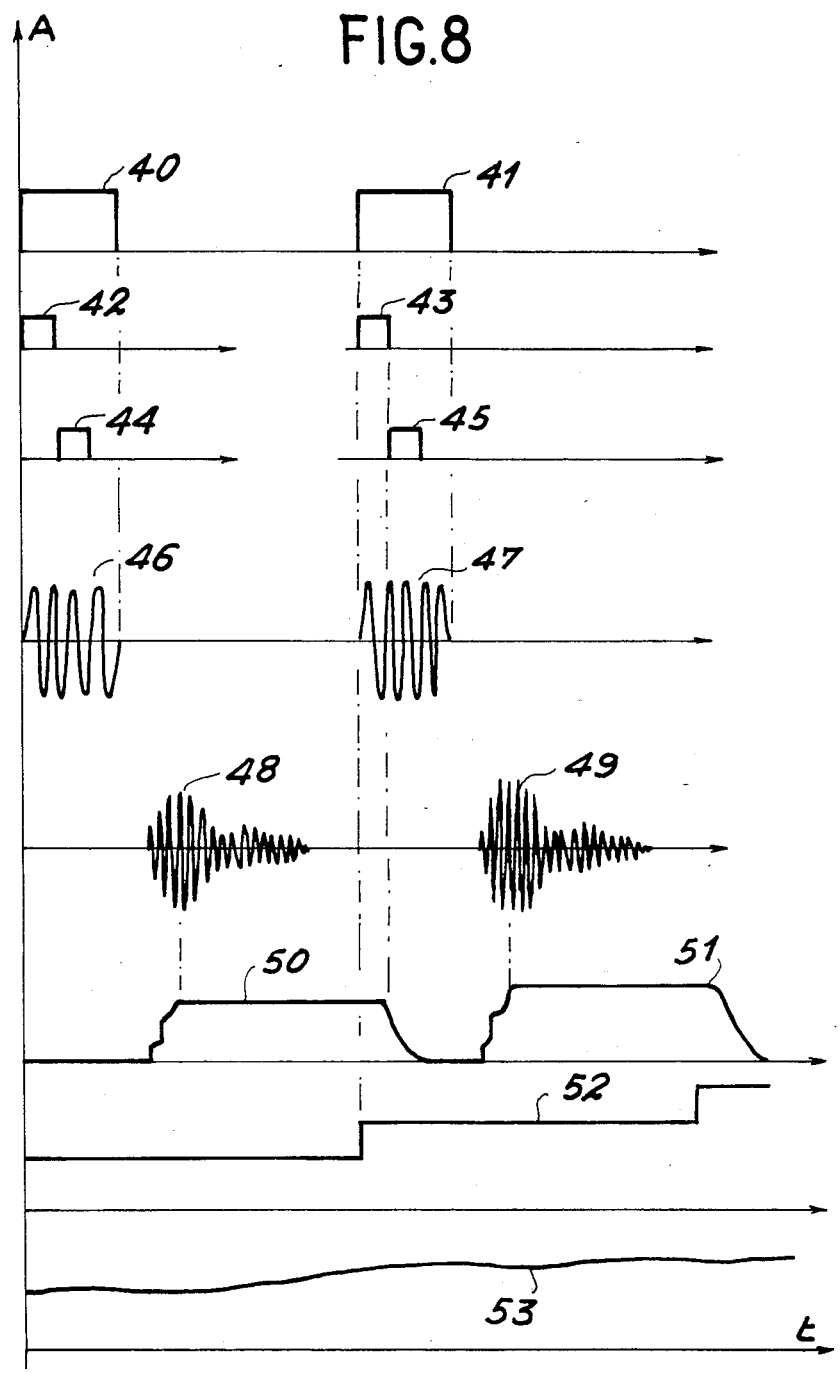

PROCESS AND APPARATUS FOR DETERMINING THE INTERFACIAL AREA IN A TWO-PHASE MIXTURE INCORPORATING A GASEOUS PHASE FLOWING IN THE FORM OF BUBBLES

BACKGROUND OF THE INVENTION

The present invention relates to two-phase mixtures incorporating a liquid phase in which flows a gaseous phase in the form of bubbles, such as is encountered e.g. in bubble columns or chemical reactors.

More specifically, it relates to the determination, in such a medium, of the value of the interfacial area, i.e. the contact surface between the gas bubbles and the liquid phase per unit of volume. Thus, the interfacial area of such a medium is a basic parameter governing the mass of heat exchanges in liquid-gas contactors of the type conventionally used in chemical engineering. Therefore, the measurement of this quantity is of vital importance for studying and checking the operation of such contactors, as well as their development.

It is pointed out that the interfacial area per volume unit, also called the specific surface, is given by the relation:

$$\gamma = (6\alpha)/D_{eq}$$

in which $\alpha$ is the vacuum level equal to the ratio of the gas volume to the total volume of gas plus liquid within the flow and $D_{eq}$ is the equivalent diameter of the gas bubbles present in the flow.

As is known, the vacuum level $\alpha$ can e.g. be measured by a manometric method, whilst the equivalent diameter of the bubbles is calculated by a photographic method.

Hitherto, there are four methods for measuring the interfacial areas of such a two-phase mixture flowing in a pipe or a stirred reactor.

The first method is a photographic method consisting of measuring the diameter of the bubbles after making a photographic negative thereof. It suffers from the disadvantage of requiring the two-phase mixture to be in a transparent container, of only permitting measurements to be carried out on groups of bubbles located close to the wall and particularly of requiring a long and tedious analysis, during which each bubble must be individually measured.

The second known method is a chemical method consisting of bringing about oxidation of an aqueous sodium sulphite solution by the oxygen contained in the gaseous phase. This method has the disadvantage of being limited to permanent flows and of requiring the use of special complementary fluids differing from those directly participating in the industrial mass or heat exchange process. Moreover, the results obtained are dependent on the geometrical shape of the contactor. In this connection, it requires a precalibration on a reference contactor, whose development and operation are far from easy. Finally, the practical performance of this chemical method is of long duration and requires several days for obtaining a correct estimate of the measured interfacial area.

The third method is an optical method using the attenuation of the intensity of a light beam passing through the container in which the two-phase mixture is flowing. This optical method has the obvious disadvantage of requiring the container to have transparent walls.

The fourth known method uses local interface detection probes, which are introduced into the gas-liquid contactor. Therefore, it suffers from the serious disadvantage of disturbing the flow which it is wished to examine, whilst also making it necessary to provide passages for the introduction of probes in the container walls or the pipe containing the two-phase flow. Finally, this method can only be used in the case of bubble columns.

SUMMARY OF THE INVENTION

The present invention specifically relates to a process for determining the interfacial area in a container containing such a flowing two-phase mixture and which makes it possible to, in a simple manner, overcome the disadvantages of the prior art of the type described hereinbefore.

In the case of the process according to the invention, for the same path of a sequence of ultrasonic sound wave trains emitted at constant amplitude in said container, the ratio of the mean values of the maximum amplitudes of the wave trains received after passing through the two-phase mixture and after passing through the liquid phase only is determined. The interfacial area is then determined by means of an experimentally plotted calibration curves giving the value of this area as a function of said ratio.

According to the invention, the use of ultrasonic procedures makes it possible to work on flows in pipes or containers having opaque walls, whilst the use of successive wave trains makes it possible to separate, on receiving said waves, each of the successively received trains without any interference between the individual trains disturbing the results. As will be explained hereinafter, the realisation of the process based on the discovery of the fact that the presence of gas bubbles flowing in a liquid does not modify the general form of the wave trains received after passing through the liquid only, but merely modifies the amplitude of the signals and particularly the peak of the first part of said signal. This relatively unexpected finding has made it possible to measure the attenuation of the peak of the signal received when the gas bubbles pass through the flow and to deduce therefrom relative to an experimentally plotted calibration curve, the exact value of the interfacial area.

In a preferred development of the process according to the invention, the sound wave trains have a wavelength clearly exceeding the diameter of the bubbles.

The invention also relates to an apparatus for performing the aforementioned process, wherein it comprises two ultrasonic transducers located at a certain distance from one another on the walls of an enclosure in contact with the two-phase mixture, one acting as a transmitter and the other as a receiver, at the outlet of the receiver and in series therewith, an amplifier, a peak detector, a sample and hold circuit and a low pass filter, a monostable circuit able to trip the sample and hold circuit for storing the maximum amplitude of each wave train, a second monostable circuit able to reset the peak detector between two consecutive wave trains and a divider for establishing the ratio of the mean values of the amplitudes of the wave trains received after passing through the two-phase mixture and after passing through the liquid phase only.

BRIEF DESCRIPTION OF THE DRAWINGS

The invention is described in greater detail hereinafter relative to non-limitative embodiments and with reference to the attached drawings, wherein show:

FIG. 8 the diagram of the different measurement and detection control pulses relative to each of the components of the apparatus according to FIG. 7.

DETAILED DESCRIPTION OF THE INVENTION

Figure 1:
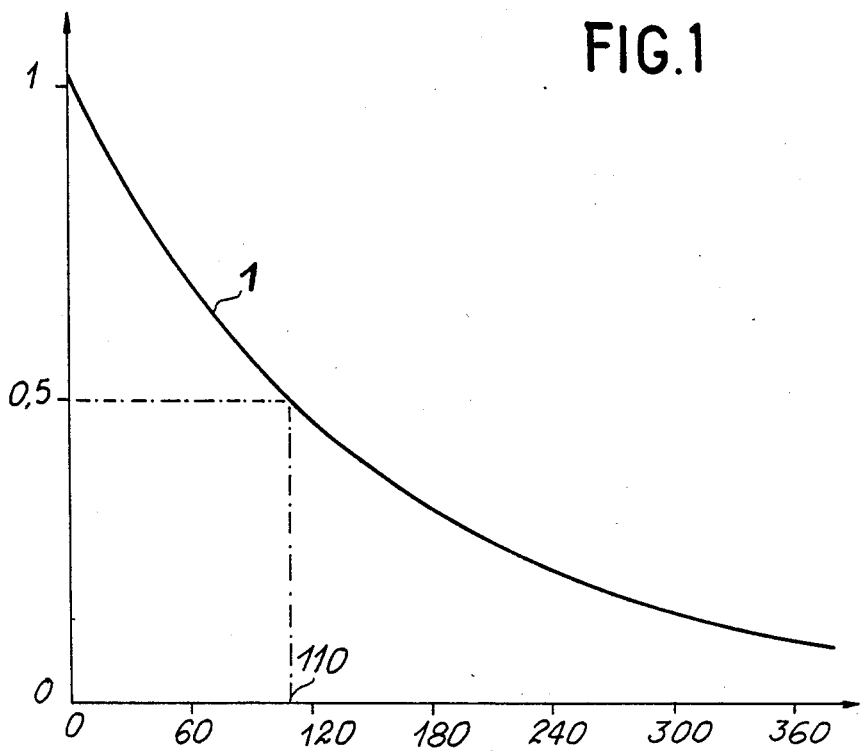
FIG. 1 the calibration curve of a standardized signal in a two-phase flow, such as is used in the process according to the invention.

FIG. 1 shows a curve calibrated by the photographic method of a standardized signal in the case of a flow of air bubbles in a volume of water. On the ordinate is plotted the ratio of the mean value of the maximum amplitudes of the wave trains received at the outlet of the two-phase mixture to the mean value of the maximum amplitudes of the wave trains received after passing through the water only. The ordinate is marked in 0, corresponding to pure air and in 1 corresponding to pure water. On the abscissa is plotted the value of the interfacial area in meters$^{-1}$, because it is in fact a specific surface per unit of volume. Curve 1 of FIG. 1 represents a continuous function decreasing from the value 1 of the standardized signal corresponding to water only and the value of this signal decreases regularly as a function of the increase in the interfacial area per unit of volume within the two-phase flow. As this function is biunivocal, it can be seen that a single value of the interfacial area corresponds to any given value of the standardized signal. For example, when the ratio of the mean values of the maximum amplitude is 0.5, FIG. 1 shows that the interfacial area value is approximately 110 m$^2$ specific surface per cubic meter of mixture. The invention consists of measuring by ultrasonic means the aforementioned ratio of the mean values of the maximum amplitudes, i.e. using a curve like that of FIG. 1 precalibrated on the mixture to be examined and ultimately the sought interfacial area value can be obtained therefrom.

In practical terms, the invention proposes two types of arrangements for the ultrasonic examination of the two-phase flow.

Figure 2:
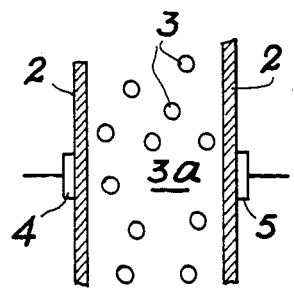
FIG. 2 diagrammatically, a first arrangement of ultrasonic transducers used for performing the process according to the invention.

FIG. 2 shows the first and simplest arrangement for small-size contactors, such as e.g. a pipe 2, whose walls are relatively close together. In this case, the gas bubbles 3 flowing in the liquid phase 3a are examined with the aid of two sound transducers which are the transmitter 4 and the receiver 5 located on either side of the walls of pipe 2 in accordance with the diameter of the latter.

Figure 3:
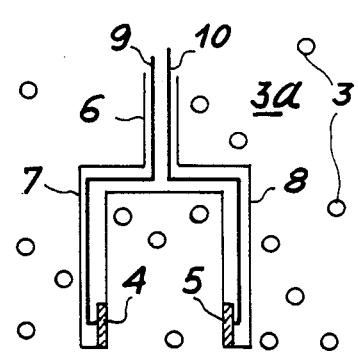
FIG. 3 a second arrangement used for large contactors making it possible to place the ultrasonic receiver and transmitter in the medium in which the flow is located.

The arrangement of FIG. 3 which is intended for large contactors has, in the same way as that according to FIG. 2, a transmitter transducer 4 and a receiver transducer 5, which are located on a fork-shaped support 6, which is immersed in the flow of bubbles 3 in liquid 3a. The lateral branches 7 and 8 of support 6 are used for the passage of two conductors 9, 10, which respectively supply transmitter 4 and receiver 5.

Figure 4:
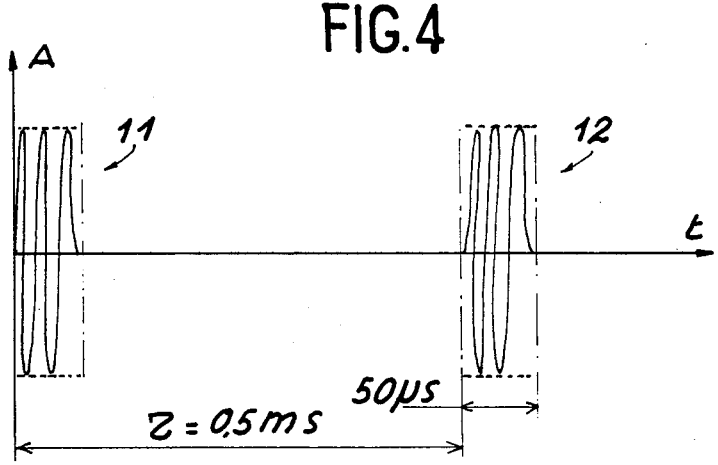
FIG. 4 the form of the wave trains in amplitude and as a function of time transmitted by the ultrasonic generator.

FIG. 4 shows the amplitude as a function of time of the ultrasonic wave trains transmitted by transmitter transducer 4. In the case of FIG. 4, there are two successive wave trains 11, 12 lasting in each case 50 microseconds and separated by 0.5 milliseconds. The oscillating frequency of the ultrasonic wave in each of the trains is approximately 750 kHz.

The interval of time between two transmitted wave trains and the duration of each train must be such that there is no superimposing of two successive trains on reception. The oscillating frequency of the ultrasonic wave of each of the trains must be such that the corresponding wavelength in the liquid clearly exceeds the diameter of the bubbles.

Figure 5:
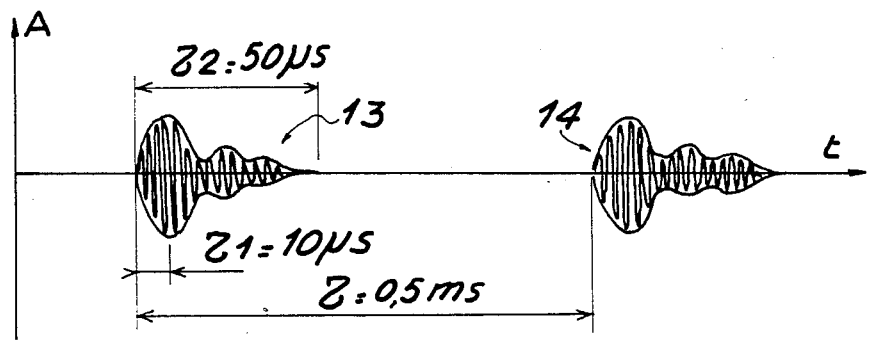
FIG. 5 the amplitudes as a function of the time of the ultrasonic signal received by the receiver transducer when there are no gas bubbles in the flow medium.

FIG. 5 shows the amplitudes as a function of time of successive wave trains received by receiver 5, after passing through the liquid with no bubbles present. It can be seen that the wave trains 13 and 14, which respectively correspond to the reception of wave trains 11, 12 in FIG. 4 are still separated by the same interval of time of 0.5 milliseconds and have the same duration of 50 microseconds. However, their form or shape is significantly modified compared with the transmitted wave train 11, 12. Thus, they comprise on the one hand a rising front lasting approximately 10 microseconds and due to the transient response time of the transducers and on the other hand, at the end of the signal, by a certain number of reflections of the wave within the medium or on the container walls.

Figure 6:
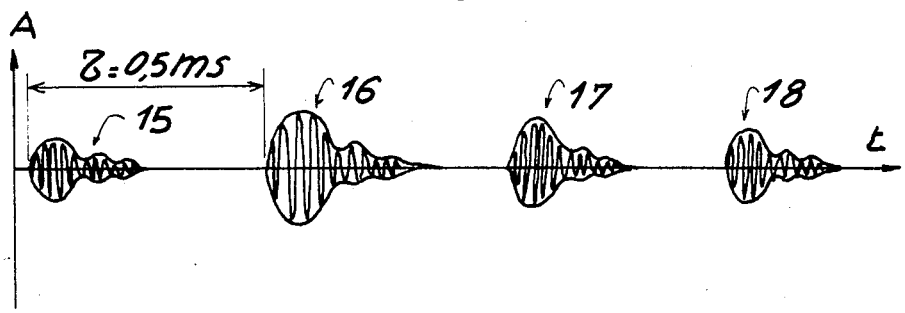
FIG. 6 the amplitudes as a function of time of the ultrasonic wave trains received by the receiver transducer, in the presence of a gas bubble flow in the investigated container.

If it is now wished to modify the physical conditions of the medium by having a flow of gas bubbles pass through it, the results visible in FIG. 6 are obtained showing the amplitudes as a function of time of the various wave trains received by transducer 5. These wave trains, which are still separated from one another by 0.5 milliseconds, all have essentially the same general form, i.e. the envelope of the signal retains the same profile. However, the signal obtained has an amplitude which is attenuated in various ways on the different wave trains 15, 16, 17 and 18 of FIG. 6, which correspond to bubble densities flowing in the liquid between two different transducers 4 and 5 at the time of the propagation of each wave train.

In practical terms, and for given vacuum levels and gas bubble sizes, it is wished to know the mean value of the maximum amplitudes of the different wave trains received, so as to compensate fluctuations between individual wave trains. The apparatus according to FIG. 7 is used for performing this measurement of the mean value of the maximum amplitude of the wave trains received.

Figure 7:
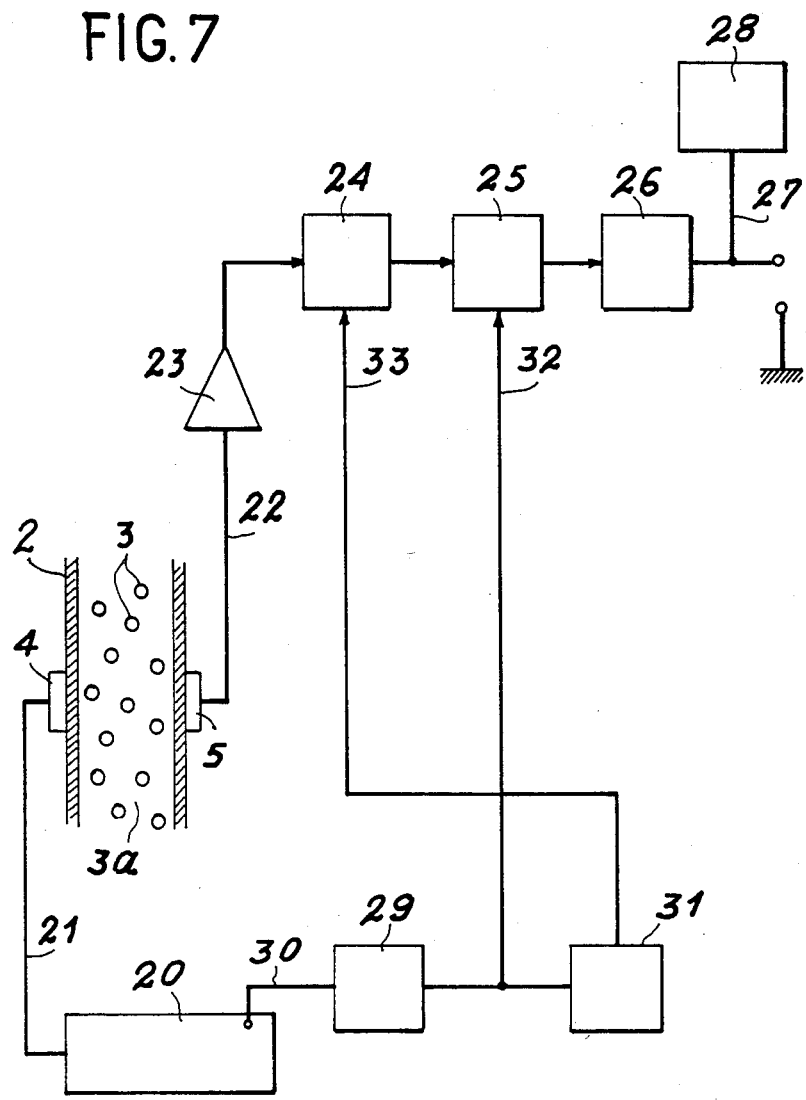
FIG. 7 diagrammatically the measuring apparatus according to the invention.

FIG. 7 shows a two-phase flow of gas bubbles 3 in a liquid 3a passing through a pipe 2. Ultrasonic transmitter 4 and ultrasonic receiver 5 are in the same position as in the arrangement of FIG. 2. The ultrasonic sound wave trains are produced by generator 20, which supplies the transmitter 4 by its line 21. At the output 22 of receiver 5 are arranged in series a current amplifier 23, followed by a peak detector 24, a sample and hold circuit 25 and a low pass filter 26. The function of peak detector 24 is to determine the maximum amplitude of a wave train received and the sample and hold circuit stores the value of this maximum amplitude. The low pass filter 26 determines the mean value of the signals collected by the sample and hold circuit 25. At the output of low pass filter 26, a conductor 27 supplies divider 28, which makes it possible to establish the ratio of the mean values determined by filter 26 on the one hand in the liquid alone in the absence of bubbles and on the other hand in the presence of the gas bubble flow.

A first monostable circuit 29 connected to the ultrasonic signal generator 20 by line 30 controls by means of line 32 the sample and hold circuit 25, whose operation it initiates for each pulse train. A second monostable circuit 31 controls, by means of conductor 33, the resetting of peak detector 24 following each recording by the sample and hold circuit 25. The two monostable circuits 29 and 31 constitute the logic part of the processing apparatus, whereas peak detector 24, sample and hold circuit 25 and low pass filter 26 are the analog part thereof, they supply electrical quantities representing the maximum amplitudes of the ultrasonic wave trains received.

It is pointed out that the ultrasonic pulse generator 20 is duplicated, namely it has a first generator which produces rectangular pulses controlling the second generator which produces sine waves. This leads to wave trains, such as will now be described relative to the diagrams of FIG. 8, which provide a better understanding of the processing of the signals. In FIG. 8, the amplitudes are plotted on the ordinate and the time on the abscissa.

In FIG. 8, it is firstly possible to see the rectangular pulses 40, 41 transmitted by the first part of ultrasonic generator 20. The two following lines show the rectangular pulses 42, 43 of the first monostable circuit 29 and the rectangular pulses 44, 45 of the second monostable circuit 31. On the following line, it is possible to see the two wave trains 46, 47 at a frequency of 750 kHz, as produced by the second part of the ultrasonic wave generator 20 and whose durations are limited by the rectangular pulses 40, 41 of the first generator. These ultrasonic wave trains 46, 47 are applied directly by conductor 21 to transmitter transducer 4. On the following line are shown at 48, 49, the wave trains received after passing through the two-phase flow by receiver 5, whereby wave train 48 corresponds to wave train 46 and wave train 49 to wave train 47. On the following line, it is possible to see how the maximum amplitudes reached by the wave trains 48, 49 are taken into account by the peak detector 24, which transforms them into constant amplitude signals 50, 51 until the corresponding pulse (in this case 45) of the second monostable circuit 31 controls the resetting of the peak detector.

On the following line, it can be seen how the sample and hold circuit 25 controlled by the pulses of the first monostable circuit 29 produces a square signal 52 representing the same maximum amplitude. At the output of low pass filter 26, signal 53 is obtained, which represents the mean value of the different amplitudes 52 recorded in the sample and hold circuit 25, following the reception of a large number of ultrasonic wave trains, such as 48 or 49. It is then merely necessary to perform the same measurement with the same apparatus in the absence of gas bubbles 3 in pipe 2 to have a different mean value for the amplitudes of the outgoing wave trains at the output of low pass filter 26 and to form the ratio of these two mean values, so that the sought value of the coefficient of the interfacial area in the examined volume can be obtained by plotting the thus found value on a precalibrated curve comparable to that of FIG. 1.

The process and apparatus according to the invention consequently has numerous applications in the development and checking of the operation of bubble contactors, such as bubble columns and stirred reactors used in chemical engineering. They also make it possible to follow the development of a two-phase flow by studying the variations of the interfacial area, which e.g. makes it possible to check the state of the flow in certain components of water nuclear reactors, as well as in pipes for transporting petroleum products.

What is claimed is:

1. A process for determining the interfacial area in a container containing a two-phase mixture incorporating a liquid phase and a gas phase flowing in the liquid phase in the form of bubbles, comprising the steps of:

emitting at constant amplitudes ultrasonic wave trains into said container;

collecting successively a first wave train received after passing through said two-phase mixture and a second wave train after passing through said liquid phase alone;

measuring the amplitude of said first and second wave trains;

calculating the mean value of the amplitude of each of said first and second wave trains;

determining the ratio of said mean values; and locating said ratio on a calibration curve to find the value of the interfacial area as a function of said ratio.

2. A process for the determination of the interfacial area according to claim 1, wherein the ultrasonic wave train has a wavelength which clearly exceeds the diameter of the bubbles.

3. An apparatus for determining the interfacial area in a container containing a two-phase mixture incorporating a liquid phase and a gas phase flowing in the liquid phase in the form of bubbles comprising:

a first ultrasonic transducer mounted on the walls of said container for transmitting ultrasonic waves into the container;

a second ultrasonic transducer mounted on the walls of said container at a distance from said first ultrasonic transducer for receiving ultrasonic waves from said first ultrasonic transducer and producing an electrical output;

an amplifier connected to said second transducer for receiving said electrical output and producing an amplified output;

a peak detector connected to said amplifier for receiving said amplified output and detecting the peak signal of said amplified output;

a sample and hold circuit connected to said peak detector for storing said peak signal;

a low pass filter connected to said sample and hold circuit for determining the mean value of said stored peak signal;

a first monostable circuit connected to said sample and hold circuit for causing said sample and hold circuit to store said peak signal;

a second monostable circuit connected to said peak detector to reset said peak detector after said peak signal is stored;

a divider connected to said low pass filter for producing a ratio of two successive mean values determined in regard to said ultrasonic waves passing first through a two-phase mixture and secondly through a liquid phase only.

* * * * *